United States Patent [19]

Borbidge et al.

[11] Patent Number: 4,740,275

[45] Date of Patent: Apr. 26, 1988

[54] DETERMINATION OF THE PARTIAL PRESSURE OF A COMPONENT OF A HOSTILE FLUID

[75] Inventors: Wendy E. Borbidge, Brunswick; Peter T. Whelan, Murrumbeena, both of Australia

[73] Assignee: Commonwealth Scientific and Industrial Research Organization, Australia

[21] Appl. No.: 627,574

[22] Filed: Jul. 3, 1984

[51] Int. Cl.[4] ............................................. G01N 27/46
[52] U.S. Cl. ................................... 204/1 T; 204/427; 204/428; 204/429
[58] Field of Search ......................... 204/1 S, 421–429, 204/406

[56] References Cited

U.S. PATENT DOCUMENTS

| 2,805,191 | 9/1957 | Hersch | 204/1 Y |
| 3,400,054 | 9/1968 | Ruka et al. | 204/1 S |
| 3,935,089 | 1/1976 | Togawa et al. | 204/429 |
| 4,007,106 | 2/1977 | Hone et al. | 204/422 |
| 4,158,166 | 6/1979 | Isenberg | 204/1 S |
| 4,207,159 | 6/1980 | Kimura et al. | 204/425 |
| 4,264,425 | 4/1981 | Kimura et al. | 204/429 |
| 4,304,652 | 12/1981 | Chiba et al. | 204/426 |
| 4,395,318 | 7/1983 | Tait et al. | 204/406 |
| 4,481,804 | 11/1984 | Eberhard et al. | 204/406 |
| 4,483,748 | 11/1984 | Yeager et al. | 204/406 |

Primary Examiner—T. Tung
Attorney, Agent, or Firm—Sughrue, Mion, Zinn, Macpeak, and Seas

[57] ABSTRACT

Apparatus and method for determining the partial pressure of a component of a fluid utilizing a probe which comprises an electrolyte with respect to the component or a constituent thereof, and to which probe the fluid is hostile. Respective interfaces of the electrolyte are disposed in contact one with the fluid and the other with a substantially non-detrimental fluid containing said component. An electric current applied between the interfaces is sufficient to transport the component through the electrolyte to said one interface and to thereby generate a local protective environment about that interface. One or more electrical parameters for the probe are continuously or periodically monitored and are utilized to derive an indication of partial pressure of the component in the hostile fluid.

3 Claims, 3 Drawing Sheets

DETERMINATION OF THE PARTIAL PRESSURE OF A COMPONENT OF A HOSTILE FLUID

This invention relates to the determination of the partial pressure of a component of a fluid hostile to the probe employed for the determination. The invention has particular but not of course exclusive application to the determination of oxygen partial pressure in a strongly reducing atmosphere.

Solid electrolyte oxygen sensors are well established as a means for determining oxygen partial pressures in gaseous and molten metal fluids. Solid electrolytes, of which partially or fully stabilized zirconia is perhaps the best known, are materials with good oxygen ion conductivity and negligible electronic conductivity. When a membrane of such a material is held with its opposite faces in contact with fluids having different oxygen potentials, an emf is established across the membrane. If one of the oxygen containing fluids is the test gas or molten metal under investigation and the other is a reference of known oxygen potential, then the emf ($E_{Nernst}$) is given by the Nernst relationship:

$$E_{Nernst} = \frac{RT}{nF} \ln \frac{pO_2 \text{ (reference)}}{pO_2 \text{ (test)}} \quad (1)$$

where
R is the gas constant
T is the absolute temperature
n in this case is 4 (the number of electrons transferred per oxygen molecule).
F is the Faraday constant and
$pO_2$ is the oxygen partial pressure This emf is measured using electrodes, reversible to the $O_2/O^{2-}$ redox equilibrium and typically a porous conductive paste, for example of platinum, placed in electrical contact with the opposing faces of the solid electrolyte membrane.

An important area of application for such probes has been to metal heat treatments, including case hardening, carbonitriding and annealing. However, a persistent problem has been the relatively short lift of standard ziroconia oxygen probes, arising from the deterioration of the outer or exposed electrode in the heavily reducing atmospheres usually encountered in heat treatment applications.

Under normal atmospheric conditions platinum is an inert noble metal, being very stable and prossessing good corrosion resistance and freedom from oxidation. However, at low oxygen pressures, platinum becomes reactive with a wide range of otherwise highly stable substances. For example, refractory oxides such as alumina and zirconia can be dissociated in the presence of platinum, resulting in the evolution of oxygen and the formation of low melting point intermetallic phases of aluminium and zirconium with platinum. This type of reaction is well known between platinum and silica, where under reducing conditions, silica can be readily converted to silicon, forming low melting point eutectic phases with platinum, as low as 830° C., leading to premature failure in the metal. Silica is a common impurity in commercial grade alumina and zirconia used for making oxygen sensors: in zirconia, the siliceous impurities tend to be concentrated in the grain boundaries of the polycrystalline ceramic.

Such reactions impose restrictions on the use of zirconia oxygen sensors with porous platinum electrodes in reducing atmospheres, where problems of poor electrode contact with the zirconia can arise. Virtually no reactions with platinum will occur if atmospheric conditions are maintained strongly oxidizing.

It is accordingly an object of the invention, in one of its particular applications, to extend the operating life of zirconia oxygen probes in highly reducing atmospheres.

The inventive concept comprises, in the particular case of an oxygen probe, the application of a current to the probe so as to pump oxygen into the hostile atmosphere and generate a protective environment about the exposed interface of the probe. Moreover, the technique relies upon an appreciation that, notwithstanding generation of the protective environment amounting to a modified local atmosphere, it is still practicable to obtain a measure of the oxygen partial pressure in the bulk atmosphere of interest.

It is known to operate ziroconia membranes in an oxygen pumping mode but not for the present purpose of generating a protective atmosphere within a hostile atmosphere, nor in conjunction with the present step of determining oxygen partial presssure in the hostile atmosphere. Prior uses of the pumping mode have included the oxygen calibration of an atmosphere (by metered pumping of oxygen into the atmosphere) and determination of oxygen or oxygen containing constituents (by pumping oxygen from the atmosphere, in some cases through a diffusion barrier). Examples of the latter application are to be found in U.S. Pat. No. 3,860,498 and U.K. Pat. No. 1,523,550. In the diffusion mode proposed in the latter patent, current through the membrane is proportional to the unkown partial pressure.

The invention accordingly provides, in one aspect, a method of determining the partial pressure of a component of a fluid utilizing a probe which comprises an electrolyte with respect to the component or a constituent thereof, and to which probe the fluid is hostile. In accordance with the method, respective interfaces of the electrolyte are disposed in contact one with the fluid and the other with a substantially non-detrimental fluid containing said component. An electric current applied between the interfaces is sufficient to transport the component through the electrolyte to said one interface and to thereby generate a local protective environment about that interface. One or more selected electrical parameters for the probe are continuously or periodically monitored and are utilized to derive an indication of partial pressure of the component in the hostile fluid.

It will be appreciated that interfaces of the solid electrolyte may not be directly in contact with the respective fluids, but may be indirectly exposed via electrodes comprising, e.g., pastes of noble metals such as platinum, gold, palladium or silver, or alloys of these elements. For measurements n gases using a gaseous reference fluid an electrode is required on each face of the solid electrolyte; for measurements in liquids such as molten metals an electrode is needed only for exposure to a gaseous reference fluid if such is employed.

The component may be oxygen and the fluid may be hostile to the probe because it is a highly reducing gaseous atmosphere. The selected electrical parameters may be voltage and resistance across said interfaces. The resistance may be measured by increasing the applied current by a small amount, and deriving the ratio of the resultant change in voltage to the change in current. The indication of the partial pressure may be derived in part by utilizing a prdetermined deviation in electric potential across said interfaces induced by application of a current substantialy equal to said applied current.

Preferably, the applied current is of a magnitude which, on being slightly increased, results in a further decrease in the observed $E_{Nernst}$.

The method may further include the ongoing control of a parameter of the hostile fluid, e.g. its temperature or the partial pressure of a component, in response to the aforedescribed determination.

Advantageously, the method further includes retarding the diffusion of the transported component from said one interface into the hostile fluid, whereby to facilitate said generation of a local protective environment.

The applied current may be adjusted in accordance with the derived indication of the partial pressure of the component in the hostile fluid.

The invention further provides apparatus for determining the partial pressure of a specific component of a fluid, wherein the apparatus includes a probe which comprises an electrolyte with respect to the component or a constituent thereof and to which probe the fluid is hostile. The apparatus further comprise means to apply between respective interfaces of the electrolyte an electric current sufficient to transport the component in question through the electrolyte to one interface and to thereby generate a local protective environment about that interface, and means to continuously or periodically monitor one or more selected electrical parameters for the probe, from which may be derived an indication of the partial pressure of the component in the hostile fluid.

The invention will now be further described, by way of example only, with reference to the accompanying drawings, in which.

Figure 1:
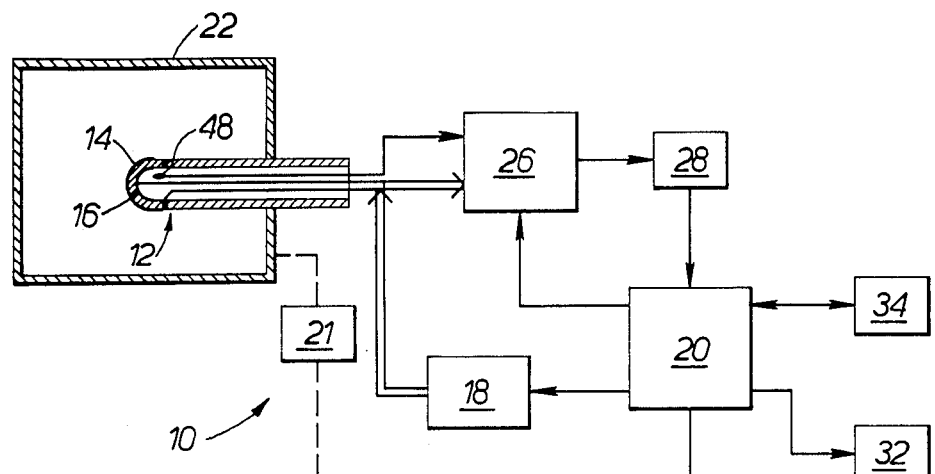
FIG. 1 is a block circuit diagram of apparatus according to the invention, utilizing a zirconia probe for the determination of oxygen partial pressure in a highly reducing atmosphere.

The arrangement 10 illustrated in FIG. 1 includes a zirconia oxygen probe 12 with an outer exposed electrode 14 and an inner reference electrode 16, a variable D.C. current source 18, and a suitable mini computer 20. Probe 12 is mounted to monitor oxygen partial pressure in a furnace 22 containing an atmosphere which is highly reducing and therefor hostile to the platinum electrodes in the presence of the refractory constituents of the probe. The temperature is continuously monitored with a suitable thermocouple element 48 within the probe.

The voltage across the probe and the thermocouple output voltage are fed to an analogue-to-digital converter 28 via a mosfet multiplexor 26 which is under computer control. The data from the A/D converter is interfaced to computer 20, if necessary using an IEEE bus, which provides a high speed bi-directional data link. Computer 20 is also provided with display means, for example a data printer 32 and/or an I/O VDU terminal 34.

Current source 18 comprises a 12 bit digital-to-analogue converter, and a power booster operational amplifier current source driven by the voltage from the converter and capable of delivering up to 1 A. This current source is capable of driving into a load that can vary over the wide impedance range typical of a zirconia probe and is controlled by the computer.

Computer 20 is any appropriate minicomputer but may conveniently be based on a 6800 microproessor and assembled from Southwest Tech Components. It is found that the associated memory should comprise about 40K of RAM and 32K of EPRROM. In a process control application, computer 20 is connected for ongoing control of a parameter of the atmosphere in furnace 22 by way of an appropriate device 21, in response to the determination of oxygen partial pressure in the atmosphere of the furnace. Typically controlled parameters might be temperature and oxygen partial pressure.

Figure 2:
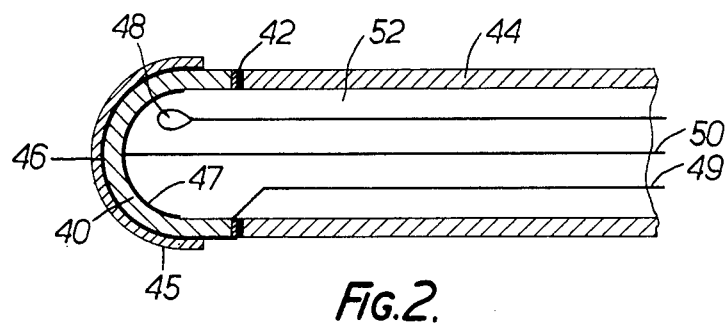
FIG. 2 is an axial cross-section of a suitable zirconia probe for use in the circuit of FIG. 1.

A suitable zirconia probe 12 is detailed in FIG. 2. This probe comprises a zirconia thimble 40 (calcia or yttria stablized) reaction bonded by an interposed platinum foil washer 42 to an alumina shank 44 of a length to suit the installation. Zirconia thimble 40 is provided with a platinum paste on both the inner and outer surfaces to form porous electrodes 47, 46 respectively. The outer electrode 46 is connected via the platinum foil to a platinum wire 49 inside the sensor, and is externally coated with a porous alumina diffusion barrier 45. Thermocouple element 48 lies adjacent the inner electrode: if appropriate the negative lead 50 of the thermocouple may be arranged to act as the inner electrode wire. The interior of the probe comprising the chamber 52 in contact with inner electrode 47 is supplied in use with a constantly slowly circulating reference atmosphere of known oxygen partial pressure and temperature, typically ambient air.

It will be noted that the zirconia probe just described which, save for diffusion barrier 45, is of a known commercial construction, is subject, by the mechanism already discussed, to serious deterioration in highly reducing atmospheres. The severity of the reactions occurring between platinum and the refractory oxides is largely controlled by the geometry of the reacting system, in particular by the amount of surface area in contact beween the reacting materials, and also by the ability of oxygen to escape from the reaction zone. These reactions are particulaly detrimental to the described reaction bonded sensor because it relies for its integrity on a solid state bond of alumina-platinum-zirconia which by its nature involves intimate contact between platinum and oxide ceramics.

Current source 18 is arranged so that the cathode of the source is connected to the inner electrode of probe 12. With this configuration, the prove will act as an oxygen pump. Current passes through the zirconia solid electrolyte in the form of oygen ion movement and through the platinum connecting electrode wires as electron flow. The environment or atmosphere in close proximity to outer electrode 46 is modified by the additional oxygen pumped through the solid electrolyte and may be considered a "micro-atmosphere" as distinct from the "bulk atmosphere" which will continue to exist in the furnace gases further removed from electrode. An equilibrium between the micro-atmosphere and the bulk atmosphere is set up, resulting in a steady total oxygen level in the system. Oxygen is taken from the micro-atmosphere into the bulk atmosphere by a combination of normal diffusion through barrier 45 and reactions between the oxygen and the components of the reducing gas atmosphere. Diffusion barrier 45 in fact acts to retard diffusion of the oxygen, thereby facilitating generation of the micro-atmosphere. It will be appreciated that the micro-atmosphere forms a local protective environment at the outer electrode interface of the zirconia because it is oxygen rich relative to the bulk reducing atmosphere.

The voltage across the probe (i.e. the voltage across the electrodes or zirconia interfaces), $V_O$, is then the sum of the Nernst emf, $E_{Nernst}$, for the micro-atmosphere and the $IR_S$ drop across the probe resistance $R_S$ (i.e. the resistance across the electrodes or zirconia interfaces), and under perfectly static conditions $E_{Nernst}$ for the micro-atmosphere can be considered to be the sum of $E_{Nernst}$ for the bulk atmosphere and a deviation $E_{dev}$, so that:

$$E_{Nernst\ (Bulk)} = V_0 - IR_S - E_{dev} \qquad (2)$$

The present invention is based on the proposition that $E_{dev}$ does not vary significantly, relative to variations in $V_0$ and $R_S$, for moderate changes in the composition and temperature of the furnace gases. Operation under changing conditions of gas composition and temperature can therefore be considered in terms of first and second order effects. The first order effects are the $R_S$ variations with temperature and $V_O$ variations with gas composition. The second order effects are the drift in $E_{dev}$ with temperature and $R_S$ variations with gas composition.

The computational technique accordingly involves the preliminary determination of a $E_{dev}$ value for particular applied current I, the repetivtive scanning of $V_0$ and $R_S$ to provide an on-going adjustment of $E_{Nernst}$ (Bulk), and redetermination of $E_{dev}$ when furnace conditions as to composition and temperature have altered to a predetermined extent.

$R_S$ is basically a combination of two components, the electrolyte resistance and the electrode resistances. The electrolyte resistance varies only with temperture and composition of the material and is independent of oxygen pressure. The electrode resistance is the most complicated parameter: it is intimately involved with the oxygen ion exchange reaction and is therefore affected by temperature, oxygen pressure, applied voltage and current, and electrode condition. Any variation in these parameters will be reflected in changes in the total DC resistance.

The resistance may be measured by an incremental technique, by varying the applied current by a small amount $\Delta I$ and measuring the corresponding change in $V_0$, $\Delta V_0$, from which $R_S = \Delta V_0 / \Delta I$. The limitation on this measurement is the effect on response time of the equivalent complex capacitive impedance of the probe. It is found, however, that for the illustrated probe of FIG. 2 the voltage stablizes within less than 50 ms at 800° C. and the technique is thus satisfactory.

$E_{dev}$ for a particular applied current level can be determined by a current scanning technique, in which the current is increased from zero in fixed increments, the probe voltage being measured and recorded at each current plateau.

As the current is increased, oxygen builds up at the outer electrode of the prove forming the micro-atmosphere as described above. At each plateau, the measurements of I and $V_0$ can be taken and used to calculate $R_S$ by the incremental method and hence the $IR_S$ drop across the probe. If there is no accumulation of oxygen at the outer electrode due to the application of the current, then:

$$V_0 = E_{Nernst\ (bulk)} + IR_S \qquad (3)$$

$E_{Nernst\ (bulk)}$ is measured at the start of the scan, with zero applied current.

In practice Equation 3 only holds true for very small currents. As the current is increased during the scan, and the micro-atmosphere becomes steadily more oxygen rich, Equation 3 begins to be in error by increasingly larger amounts, i.e., $$E_{Nernst\ (bulk)} = V_0 - IR_S - E_{dev} \qquad (2)$$

The value of $E_{dev}$ is equivalent to the amount that the Nernst voltage of the bulk atmosphere has been modified by changes in the micro-atmosphere due to the build-up of oxygen for a particulary value of applied current I. The relationship between I and $E_{dev}$ can be expected to vary with temperture, electrode condition and gross changes in gas flow rate and composition of the bulk atmosphere in the furnace. For this reason, it is necessary to re-initiate current scans at periodic intervals, as these conditions vary with time.

Desirably, computer 20 is arranged to measure and calculate $R_S$ several times a second and to thus obtain a rapid up-dating of oxygen partial pressure. It will be appreciated that the arrangement of FIG. 1 can thereby be employed for underlying process control, the computer determining the appropriate I for a sufficient protective micro-atmosphere give the oxygen partial pressure in the furnace gases (the bulk atmosphere), and periodically up-date the $E_{dev}$ value for the chosen I and rapidly and continuously monitoring $V_0$ and $R_S$ to provide an accurate on-going determination of oxygen partial pressure in the furnace. The applied current I would be adjusted in accordance with the derived $E_{Nernst\ (Bulk)}$ to optimize protection of the probe.

It has been found that there is a clear limit on the magnitude of the current which can be applied without detriment to the probe. As current is increased, the observed $E_{Nernst}$ for the micro-atmosphere tends to be less than $E_{Nernst\ (Bulk)}$, but not indefinitely. A current is eventually reached, $I_{break-point}$, at which the deviation changes polarity and in fact goes sharply positive with further increases in applied current. For example, operating a probe of the form of FIG. 2 at 900° C. in a reducing atmosphere provided by commercial grade 10% hydrogen and nitrogen, the oxygen partial pressure of which was of the order of $10^{-18}$ atmospheres, the turning point was obserbed in the vicinity of 20 mA and the deviation became positive at about 26 mA. The detailed results are demonstrated by FIGS. 4A and 4B.

Figure 4A:
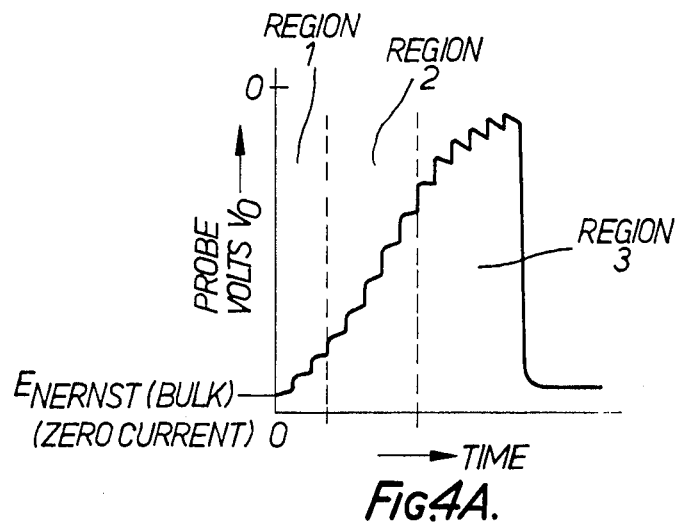
FIGS. 4A and 4B respectively show an exemplary voltage transfer characteristic for a current scan, and the corresponding plot of $E_{dev}$ against current magnitude.
Figure 4B:
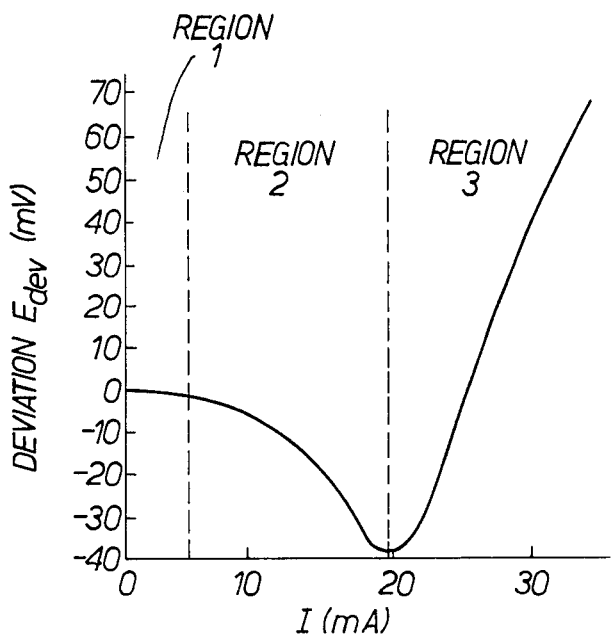

Three distinct stages are evident in FIGS. 4A and 4B. For very small applied current levels (zero and the first two or three steps of the scan) the probe is effectively acting as a linear resistance, producing an IR drop proportional to the current. The oxygen evolved at the outer electrode is being dispersed into the bulk atmosphere at such a rate as to have no appreciable effect on the calculated Nernst voltage (that is, $E_{nernst\ (micro)} \approx E_{Nernst\ (bulk)}$). Because this region shows no non-ohmic characteristics both electrodes can be assumed not to be rate-limiting and the exchange reaction (2) fully applies, that is ionic current is the only mechanism of charge movement. At these low current levels the micro-atmosphere has not been created to the extent which can be detected by the probe.

At slightly higher current levels of the scan the probe resistance appears to become non-ohmic in character. The effect observed is that of an increasing IR drop with increasing applied current, that is the probe resistance is increasing with current.

The rise in resistance, as measured by the incremental $\Delta I$, $\Delta V$ method, could be explained in two ways. One explanation is that electrodes of a fixed porosity tend to impose an increasing restriction upon the transfer of oxygen as the current is increased. This may be occurring to some extent; however the increasing magnitude of the $E_{dev}$ in this region of the scan suggests that the dominant cause of the apparent resistance rise is a decreasing value of Nernst voltage; with increasing current the oxygen evolved at the outer electrode is forming an oxygen rich micro-atmosphere around the probe, that is $E_{Nernst\ (micro)}\ E_{Nernst\ (bulk)}$. By the nature of the $\Delta I/\Delta V$ method of resistance measurement, an apparent increase in resistance will occur if the Nernst voltage is decreasing in magnitude as the current is incremented during a scan.

It is most probable therefore that at these current levels in the middle range of the scan, the probe is still obeying the exchange reaction and that the non-linearity shown in FIGS. 4A and 4B is due to modification of the micro-atmosphere by oxygen evolved at the outer electrode.

At the high current end of the scan a marked change in character can be observed, which corresponds to a descrease in the IR drop across the probe with increasing current. The decreasing resistance in this most distinctly non-linear section of the scan implies that there is some change occurring in the mechanism of current flow.

It is thought likely that the observed turning point is a result of direct electron injection at high applied potentials: with increasing applied current, no further oxygen is evolved at the outer electrode, and the micro-atmosphere ceases to become more oxidizing. The exchange reaction is no longer obeyed fully for higher currents and further current through the electrolyte is via electron rather than oxygen ion flow. Further tests have suggested that there is a marked deterioration of the probe if the applied current is set for any extended period above the value at which the deviations become positive.

From these observations, it is considered desirable that the applied current is of a magnitude which, on being slightly increased, results in a further decrease in the observed $E_{Nernst}$, i.e. an increase in the negative magnitude of $E_{dev}$.

Figure 3:
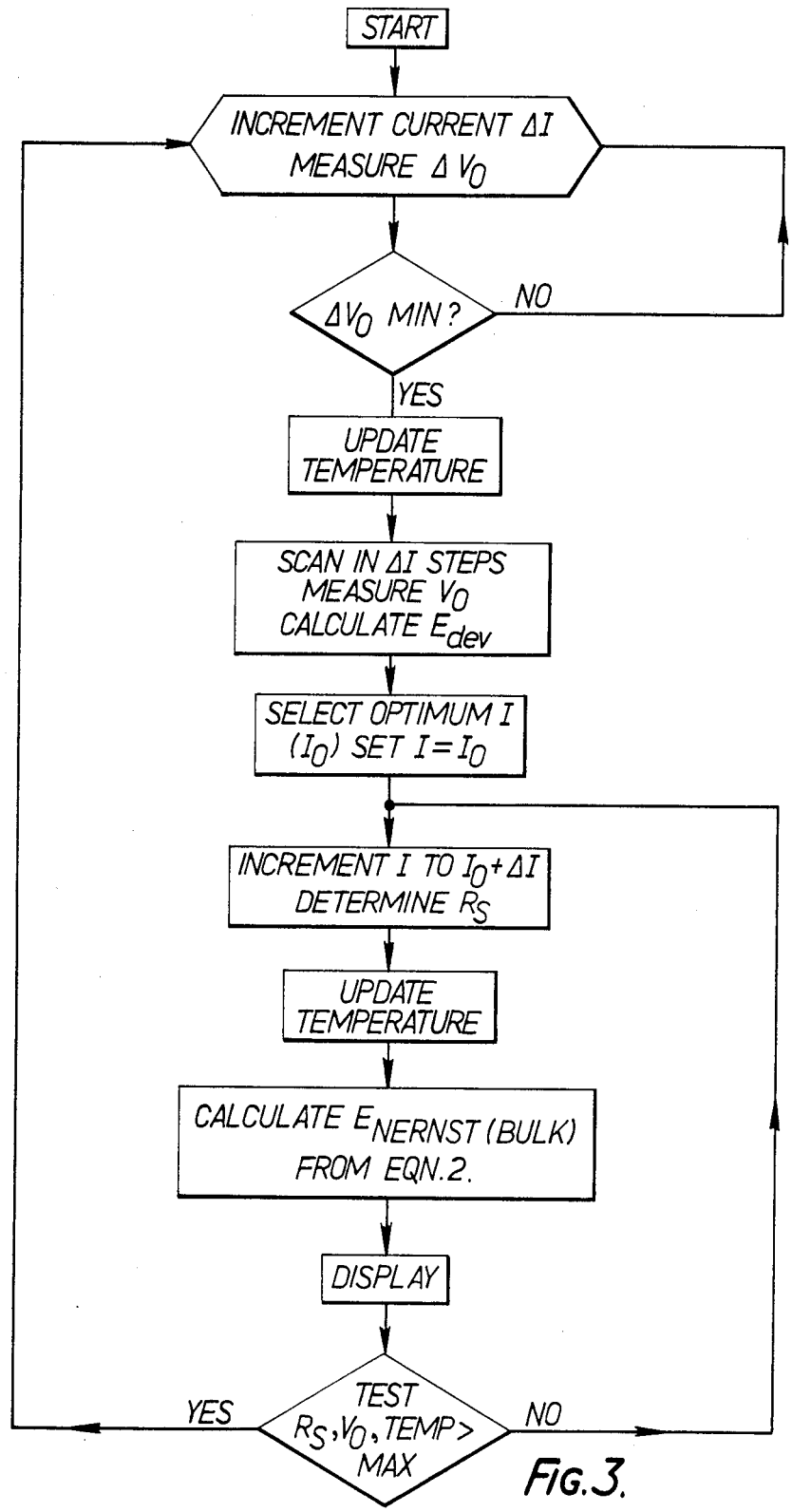
FIG. 3 is a flow chart setting out the control and computational steps during operation of the apparatus of FIG. 1.

FIG. 3 is a flow chart for the sensing and analysis steps carried out by computer 20.

We claim:

1. A method of determining the partial pressure of oxygen in a strongly reducing gaseous atmosphere utilizing a probe connected to a circuit and comprising an electrolyte of zirconia with respective electrodes one of which is a reference electrode in contact with a gas of known oxygen partial pressure and the other is a sensing electrode in contact with said atmosphere, the method comprising the steps of:

from time to time determining values of the deviation ($E_{dev}$) in the Nernst voltage caused by an applied electric current (I) effective to pump oxygen ions through said electrolyte from the reference electrode to the sensing electrode, wherein said determination is carried out by increasing said applied current by small increments through a succession of values, determining the voltage (V) and the resistance (R) between said electrodes at at least one of said values, and calculating $E_{dev}$ as the change in the Nernst voltage relative to zero applied current;

applying a constant electric current between said electrodes to pump oxygen ions through said electrolyte from the reference electrode to the sensing electrode, the value ($I_o$) of said constant electric current being selected to create a micro atmosphere of oxygen around the sensing electrode to form a local protective environment to prevent deterioration of the electrode by contact with the strongly reducing gaseous atmosphere;

measuring the resistance ($R_s$) and voltage ($V_o$) between said electrodes while applying current $I_o$; and deriving an indication of the partial pressure of the oxygen in the strongly reducing gaseous atmosphere by calculating the Nernst voltage for said atmosphere, $E_{Nernst}$, in accordance with the following formula:

$$E_{Nernst} = V_o - I_o R_s - E_{dev(Io)}$$

Where:
$E_{dev(Io)}$ is the deviation in the Nernst voltage caused by said applied current of value $I_o$, derived from the said determined value(s) of $E_{dev}$.

2. A method according to claim 1 further comprising retarding the diffusing of the oxygen into said strongly reducing gaseous atmosphere by means of a diffusion barrier of porous material around said sensing electrode, thereby to enhance creation of said micro-atmosphere of oxygen over the sensing electrode.

3. A method according to claim 1 wherein, in the determination of values for $E_{dev}$ and in measuring resistance $R_s$, the resistance is measured by increasing the applied current by a small increment and deriving the ratio of the resultant change in voltage to the change in current.

* * * * *